(12) United States Patent
Urata et al.

(10) Patent No.: US 6,172,267 B1
(45) Date of Patent: Jan. 9, 2001

(54) PROCESS FOR PRODUCING ALDEHYDES AND BISPHOSPHITE COMPOUND TO BE USED FOR THE PROCESS

(75) Inventors: Hisao Urata; Yasuhiro Wada, both of Kanagawa; Yoshiyuki Tanaka, Kangawa; Naoki Suzuki, Kurashiki; Hiroaki Itagaki, Kanagawa, all of (JP)

(73) Assignee: Mitsubishi Chemical Corporation, Tokyo (JP)

( * ) Notice: Under 35 U.S.C. 154(b), the term of this patent shall be extended for 0 days.

(21) Appl. No.: 09/179,187

(22) Filed: Oct. 27, 1998

(30) Foreign Application Priority Data

Oct. 28, 1997 (JP) .................................................. 9-295496

(51) Int. Cl.⁷ .................................................. C07C 45/49
(52) U.S. Cl. ........................................... 568/454; 568/451
(58) Field of Search .................... 568/451, 454; 558/73, 85

(56) References Cited

U.S. PATENT DOCUMENTS

| | | | |
|---|---|---|---|
| 4,159,999 | * 7/1979 | Stautzenberger | 568/454 |
| 4,694,109 | * 9/1987 | Devon | 568/454 |
| 4,769,498 | * 9/1988 | Billig | 568/454 |
| 4,885,401 | * 12/1989 | Billig | 568/454 |
| 5,113,022 | * 5/1992 | Abatjoglou | 568/454 |
| 5,202,297 | * 4/1993 | Lorz | 502/106 |
| 5,254,741 | * 10/1993 | Lorz | 568/454 |
| 5,288,918 | 2/1994 | Maher et al. . | |
| 5,312,996 | 5/1994 | Packett . | |
| 5,364,950 | 11/1994 | Babin et al. . | |
| 5,512,695 | 4/1996 | Kreutzer et al. . | |
| 5,512,696 | 4/1996 | Kreutzer et al. . | |
| 5,663,369 | 9/1997 | Kreutzer et al. . | |
| 5,672,766 | * 9/1997 | Mori | 568/454 |
| 5,696,280 | 12/1997 | Shapiro . | |
| 5,756,855 | * 5/1998 | Abatjoglou | 568/454 |
| 5,767,321 | * 6/1998 | Billig | 568/454 |
| 5,821,378 | 10/1998 | Foo et al. . | |
| 5,886,237 | * 3/1999 | Packett | 568/454 |

FOREIGN PATENT DOCUMENTS 8-165266 * 6/1996 (JP) .

OTHER PUBLICATIONS

CA:125:195001 abs of JP08165266, Jun. 1996.*
English Abstract of WO 97/39997, Oct. 30, 1997.
English Abstract of WO 97/36856, Oct. 9, 1997.

* cited by examiner

Primary Examiner—Jean F Vollano

(57) ABSTRACT

A process for producing aldehydes, which comprises reacting a mono-olefinic compound with carbon monoxide and hydrogen in the presence of a Group VIII transition metal compound of a bisphosphite compound of the following formula (1) or (2)

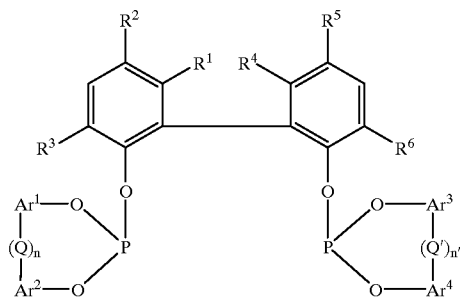

(1)

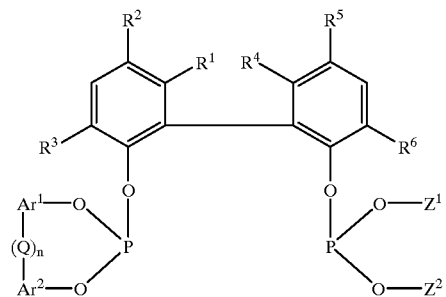

(2)

11 Claims, 6 Drawing Sheets

DHA = 0°   DHA = 180°

$$Y = 1.31 \times 10^{-3} X^2 - 0.24X + 11.1$$

$$Y = 3.55 \times 10^{-3} X^2 - 0.64X + 28.6$$

PROCESS FOR PRODUCING ALDEHYDES AND BISPHOSPHITE COMPOUND TO BE USED FOR THE PROCESS

BACKGROUND OF THE INVENTION

1. Field of the Invention

The present invention relates to a process for producing aldehydes by hydroformylation of a mono-olefinic compound.

2. Discussion of Background

A process which comprises reacting an olefinic compound with water gas in the presence of a catalyst to produce aldehydes or alcohols as their hydrogenated products, is well-known as a hydroformylation process. As a catalyst for the hydroformylation reaction, it is common to use a soluble complex of Group VIII metal and an organic phosphorous compound as a ligand. In general, the ligand used together with the metal component of the catalyst gives a substantial influence to the catalytic reaction. Also in the hydroformylation reaction, it is well known that the catalytic activity and the selectivity are substantially influenced by the ligand. On the other hand, in order to carry out the hydroformylation reaction industrially advantageously, it is required not only to improve the catalytic activity and selectivity but also to maintain the ligand to be stable so as not to let a decomposition reaction of the ligand including a modification reaction such as a structural change take place during the entire process for the production of aldehydes. Accordingly, various efforts to design the ligand have been made for these purposes.

Various phosphite compounds are known as a group of phosphorus compounds which may be used as the ligands for the hydroformylation reaction. In addition to simple monophosphites such as trialkyl phosphites or triarylphosphites, various phosphite compounds such as polyphosphites having a plurality of coordinating phosphorus atoms in their molecules, have been proposed. For example, JP-A-62-116587 or JP-A-6-166694 discloses a hydroformylation reaction using a bisphosphite compound wherein one of the two phosphite groups has a cyclic structure, and JP-A-62-116535, JP-A-2-231497, JP-A-6-199728 or JP-A-6-199729 discloses a hydroformylation reaction employing a bisphosphite compound wherein both of the two phosphite groups have cyclic structures. In the bisphosphite compounds used in these prior art references, 6,6'-positions of the bisarylene group as the crosslinking moiety have no substituents.

JP-A-6-184036 discloses a method for producing 1,6-hexanedials by a hydroformylation reaction of a diene such as butadiene by using a bisphosphite wherein the 6,6'-positions of the bisarylene group as the crosslinking moiety have substituents, and both of the two phosphite groups have cyclic structures. However, nothing is disclosed with respect to the function of such a bisphosphite in the hydroformylation reaction of a mono-olefin, and there is no disclosure of the stability of the bisphosphite compound.

Thus, various phosphite compounds have been proposed as ligands to be used for the hydroformylation reaction, but none of them is fully satisfactory with respect to the stability or the reactivity for the hydroformylation reaction of a mono-olefinic compound.

As described above, heretofore, various bisphosphite compounds have been proposed as ligands to be used for the hydroformylation reaction, and in the hydroformylation reaction employing such compounds, it is possible to obtain characteristic results of the reaction depending upon the structures of the bisphosphite compounds. However, it has been impossible to simultaneously satisfy a high reaction rate and a high stability of the ligands and the economical efficiency tends to be poor in a commercial production. Therefore, there has been a problem that they can hardly be used as catalysts for industrial purposes. Accordingly, it has been desired to develop a bisphosphite ligand which has excellent stability of the ligand not only in the hydroformylation reaction zone but also in the entire process, while maintaining a high reaction rate.

SUMMARY OF THE INVENTION

In the course of a research for a ligand useful to improve or maintain the reaction activity in the hydroformylation reaction and the stability of the ligand not only in the hydroformylation reaction zone but also in the subsequent step, specifically the distillation step for separation of aldehydes, the present inventors have found that a bisphosphite compound having a specific structure is excellent particularly in the thermal stability, and when it is used as a component of the catalyst in the hydroformylation reaction i.e. as a ligand to be used together with the metal component of the catalyst, the reaction will proceed at a high speed, and the ligand will remain to be stable even in the distillation step for the recovery of aldehydes. The present invention has been accomplished on the basis of this discovery.

Namely, in the first aspect, the present invention provides a process for producing aldehydes, which comprises reacting a mono-olefinic compound with carbon monoxide and hydrogen in the presence of a Group VIII transition metal compound, wherein the reaction is carried out in the presence of a bisphosphite compound of the following formula (1) or (2) having a bisphenylene structural moiety connecting the two phosphite structures, said bisphenylene structural moiety being such that when it is represented by a structure of the following formula (I) as a model, and when, by the following calculation method, using a dihedral angle between the two aromatic rings of the structure of the formula (I) as a variable $X$ (degrees), energy values are calculated by changing the dihedral angle $X$ within a range of from 130 to 40 degrees, and relative energy values $Y$ (kcal/mol) are calculated by subtracting the lowest calculated energy value from the energy values at the respective dihedral angles, whereupon the relation between the dihedral angle $X$ and the relative energy value $Y$ is represented by an approximate formula of $Y = AX^2 + BX + C$, the coefficient A satisfies $A \geq 5 \times 10^{-4}$:

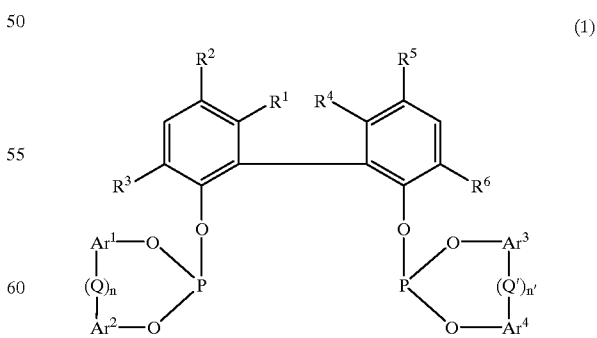

wherein each of $R^1$ to $R^6$ which are independent of one another, is a group selected from an organic group, an inorganic group and a halogen atom, each of $Ar^1$, $Ar^2$, $Ar^3$ and $Ar^4$ which are independent of one another, is a substituted or unsubstituted arylene group, each of Q and Qu which are independent of each other, is a linking group selected from the group consisting of —CR$^7$R$^8$—, —O—, —S—, —NR$^9$—, —SiR$^{10}$R$^{11}$— and —CO— (wherein each of R$^7$ to R$^{11}$ which are independent of one another, is a hydrogen atom, a C$_{1-12}$ alkyl group or an aryl group), and each of n and n' which are independent of each other, is 0 or 1,

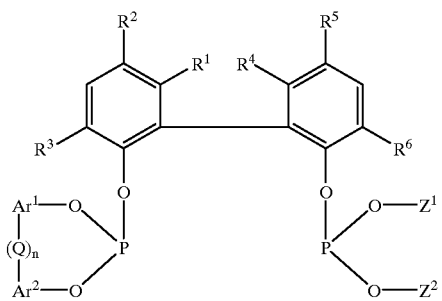

(2)

wherein R$^1$ to R$^6$, Ar$^1$ to Ar$^2$, Q and n are as defined in the formula (1), each of Z$^1$ and Z$^2$ which are independent of each other, is a C$_{1-20}$ alkyl group, a cycloalkyl group, a substituted or unsubstituted aryl group, an aralkyl group or a hetero aryl group,

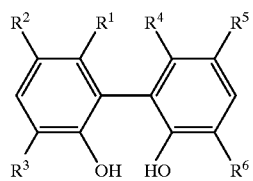

(I)

Calculation Method

Calculation method: Molecular Mechanics Method

Program: CAChe Mechanics Release 3.9

Details of calculation: Optimization Method: Block-Diagonal

Newton Raphson Method

Converging condition: 0.001 kcal/mol.

In the second aspect, the present invention provides a process for producing aldehydes, which comprises reacting a mono-olefinic compound with carbon monoxide and hydrogen in the presence of a Group VIII transition metal compound, wherein the reaction is carried out in the presence of a bisphosphite compound of the following formula (1) or (2):

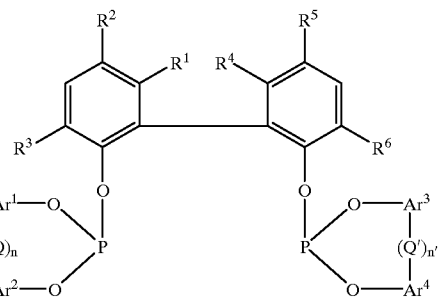

(1)

wherein each of R$^1$ and R$^4$ which are independent of each other, is a C$_{1-12}$ alkyl group, a cycloalkyl group, an alkoxy group, a silyl group, a siloxy group or a halogen atom, each of R$^2$, R$^3$, R$^5$ and R$^6$ which are independent of one another, is a hydrogen atom, a C$_{1-20}$ alkyl group, a cycloalkyl group, an alkoxy group, an aryl group, a silyl group or a siloxy group, each of Ar$^1$, Ar$^2$, Ar$^3$ and Ar$^4$ which are independent of one another, is a substituted or unsubstituted arylene group, each of Q and Q' which are independent of each other, is a linking group selected from the group consisting of —CR$^7$R$^8$—, —O—, —S—, NR$^9$—, —SiR$^{10}$R$^{11}$— and —CO— (wherein each of R$^7$ to R$^{11}$ which are independent of one another, is a hydrogen atom, a C$_{1-12}$ alkyl group or an aryl group), and each of n and n' which are independent of each other, is 0 or 1,

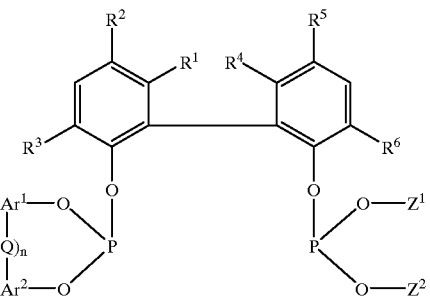

(2)

wherein R$^1$ to R$^6$, Ar$^1$ to Ar$^2$, Q and n are as defined in the formula (1), each of Z$^1$ and Z$^2$ which are independent of each other, is a C$_{1-20}$ alkyl group, a cycloalkyl group, a substituted or unsubstituted aryl group, an aralkyl group or a hetero aryl group In the third aspect, the present invention provides a novel bisphosphite compound of the formula (2).

DETAILED DESCRIPTION OF THE PREFERRED EMBODIMENTS

Now, the present invention will be described in detail.

The process of the present invention is carried out in the presence of a bisphosphite compound of the above mentioned formula (1) or (2). The bisphosphite compound of the formula (2) is novel.

Figure 1:
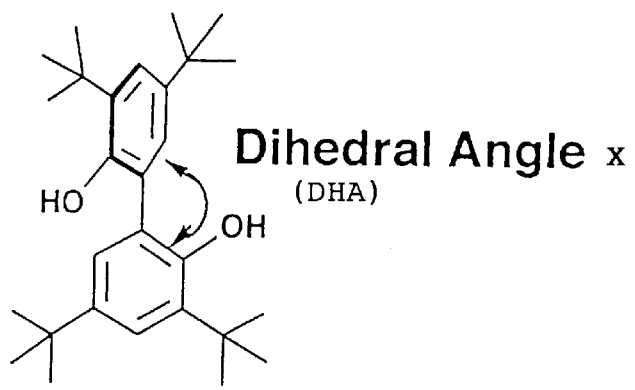
FIG. 1 schematically illustrates the dihedral angle (DHA) between the two aromatic rings in the structure of the formula (I).
Figure 2:
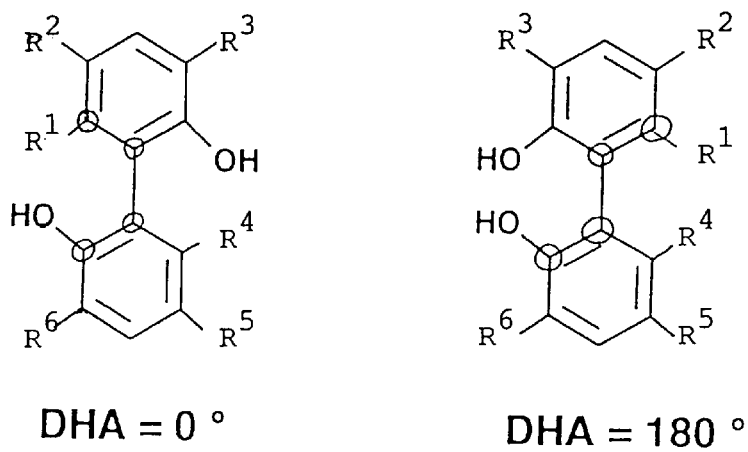
FIG. 2 schematically illustrates structures wherein DHA is 0° and 180°, respectively.

Specifically, the present invention relates to a bisphosphite compound of the above formula (1) or (2) which is characterized by the bisphenylene structural moiety connecting the two phosphite structures, which is represented by a structure of the above formula (I) as a model. And, when, by the following calculation method, using a dihedral angle between the two aromatic rings of the structure of the formula (I) as a variable X (degrees), energy values of the molecule are calculated by changing the dihedral angle X within a range of from 130 to 40 degrees, a relative energy value obtained by subtracting the lowest calculated energy value from the energy value at each dihedral angle, is represented by Y (kcal/mol). The dihedral angle (DHA) between the two aromatic rings in the formula (I) is schematically illustrated in FIGS. 1 and 2. The relation between the dihedral angle X and the relative energy value Y can be represented by an approximate formula $Y=AX^2+BX+C$, and the present invention relates to a bisphosphite compound containing a bisphenylene structural moiety wherein the coefficient A in this approximate formula satisfies $A \geq 5 \times 10^{-4}$.

Calculation Method

Calculation method: Molecular Mechanics Method
Program: CAChe Mechanics Release 3.9
Details of calculation: Optimization Method: Block-Diagonal
Newton Raphson Method
Converging condition: 0.001 kcal/mol In the above approximate formula of $Y=AX^2+BX+C$, the coefficient A indicates the difficulty or easiness of the change of the dihedral angle. For example, as A increases, the dihedral angle of the compound of the formula (I) tends to hardly change from the value of the dihedral angle which gives the lowest energy value. The coefficient A is not influenced by the manner of setting the dihedral angle X and is a coefficient which can be straight forwardly obtained by the above mentioned calculation method with respect to a certain bisphenol compound of the formula (I).

The present invention is based on a discovery that the coefficient A in the above mentioned approximate formula is related to the stability of the bisphosphite ligand, and a bisphosphite compound whereby the coefficient A is within the specified range, is capable of maintaining a high reaction rate when used as a ligand in the hydroformylation reaction of a mono-olefin and capable of remaining to be thermally stable throughout the entire process. In the present invention, the bisphosphite compound may be any compound so long as the above coefficient A satisfies $A \geq 5 \times 10^{-4}$. However, a compound whereby A is within a range of $1.00 \times 10^{-3} \leq A \leq 1.0 \times 10^{-2}$, especially $1.20 \times 10^{-3} \leq A \leq 0.8 \times 10^{-2}$, is particularly preferred form the viewpoint of the thermal stability.

The present invention is by no means restricted by a theory, but it may be mentioned that in general, when a bisphosphite compound as represented by the formula (1) or (2) is exposed under a heating condition, the thermal energy is transmitted to its molecules, whereby the motion of the entire molecules will be activated. By the activation, the molecular motion will be initiated. Here, it is believed that the higher degree of freedom of the molecules themselves enable a release of the molecular energy, resulting in the higher thermal stability. In such a case, as possible molecular motions, there may be mentioned rotation of the carbon—carbon bond linking the two phenylene groups in the bisphenol structure of the formula (I) crosslinking the two phosphorus atoms, and motions of cyclic structures containing the phosphorus atoms. A compound having a structure whereby the molecular motion can readily be carried out by carrying out the rotation of the carbon—carbon bond smoothly, has been believed to be thermally stable as the entire molecules. However, surprisingly, the present inventors have found that the contrary to the conventional belief, the stability is higher with a compound wherein the change in the molecular structure is small. As a result of detailed studies, it has been found that the reaction whereby the bisphosphite undergoes decomposition by a structural change, proceeds in a state where it is coordinated to the Group VIII transition metal, and it is accordingly assumed that by restricting the free rotation of the substituted bisphenol structure in the bisphosphite, the complex tends to hardly have a structure (conformation) which induces the decomposition of the bisphosphite coordinated to the Group VIII transition metal compound. As a result, the stability of the bisphosphite as the ligand is believed to increase. Accordingly, as a means to evaluate the stability of the bisphosphite compound, a method has been devised to examine the correlation between the relative energy value Y and the dihedral angle X between the two aromatic rings in the bisphenylene structural moiety of the bisphosphite compound.

Thus, in the present invention, the calculation is carried out by setting a model structure like the formula (I). The stability of the compound by this model structure is believed to sufficiently represent the stability of the Rh complex in the hydroformylation reaction system.

The bisphosphite compound of the present invention has ring structures at the terminals of the molecule and is accordingly assumed to be a thermally unstable compound as the strain formed in the molecule tends to be hardly relaxed as compared with a compound having non-cyclic structures at both terminals of the molecule. Even with such an unstable compound, by selecting a bisphosphite compound having a specific structure as in the present invention, it becomes possible to provide a ligand which is sufficiently practically useful on an industrial scale.

In the above formula (1) or (2), each of $R^1$ to $R^6$ which are independent of one another, is a group selected from an organic group, an inorganic group and a halogen atom. The organic group may, for example, be a hydrogen atom, an alkyl group, a cycloalkyl group, an alkoxy group, a trialkylsilyl group, a trialkylsiloxy group, an alkoxy carbonyl group or an acyl group. The inorganic group may, for example, be a —$SO_3Na$ group, a —$SO_3Li$ group, or a —$COONa$ group. The halogen atom may be a fluorine atom, a chlorine atom, a bromine atom or an iodine atom.

Specifically, each of $R^1$ and $R^4$ may, for example, be a $C_{1-12}$ linear or branched alkyl group such as a methyl group, an ethyl group, a n-propyl group, an isopropyl group, a t-butyl group or a decyl group, a $C_{3-12}$ cycloalkyl group such as a cyclopropyl group or a cyclohexyl group, a $C_{1-12}$ alkoxy group such as a methoxy group, an ethoxy group or a t-butoxy group, a silyl group such as a trimethylsilyl group, a siloxy group such as a trimethyl siloxy group, an alkoxy carbonyl group such as an ethoxy carbonyl group or an isopropoxy carbonyl group, an acyl group such as an acetyl group, a —$SO_3Na$ group, a —$SO_3Li$ group, a —$COONa$ group or a halogen atom such as a chlorine atom, a fluorine atom, a bromine atom or an iodine atom. Among them, preferred is a $C_{1-3}$ lower alkyl group such as a methyl group or an ethyl group, a $C_{1-3}$ lower alkoxy group such as a methoxy group or an ethoxy group, or a halogen atom such as chlorine atom, and particularly preferred is a methyl group or a methoxy group. Each of $R^2$, $R^3$, $R^5$ and $R^6$ may, for example, be a $C_{1-20}$ linear or branched alkyl group such as a methyl group, an ethyl group, a propyl group, an isopropyl group, a butyl group, a t-butyl group, a t-pentyl group, a t-hexyl group, a nonyl group or a decyl group, a $C_{3-20}$ cycloalkyl group such as a cyclopropyl group or a cyclohexyl group, a $C_{1-20}$ alkoxy group such as a methoxy group, an ethoxy group or a t-butoxy group, an aryl group such as a phenyl group or a p-tolyl group, a silyl group such as a trimethylsilyl group, or a siloxy group such as a trimethylsiloxy group. Among them, preferred is a $C_{3-20}$, more preferably $C_{3-10}$, branched alkyl or cycloalkyl group such as an isopropyl group, a t-butyl group, a t-pentyl group, a t-hexyl group, a cyclopropyl group or a cyclohexyl group.

Preferred examples of the bisarylene group of the formula:

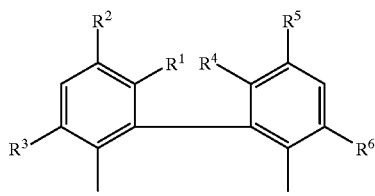

(wherein each of $R^1$ to $R^6$ are as defined above in the formula (1) or (2)) as the crosslinking structural moiety of the formula (1) and (2), include a 3,3-di-t-butyl-5,5',6,6'-tetramethyl-1,1'-biphenyl-2,2'-diyl group, a 3,3',5,5'-tetra-t-butyl-6,6'-dimethyl-1,1'-biphenyl-2,2'-diyl group, a 3,3',5,5'-tetra-t-pentyl-6,6'-dimethyl-1,1'-biphenyl-2,2'-diyl group, a 3,3',5,5'-tetra-t-hexyl-6,6'-dimethyl-1,1'-biphenyl-2,2'-diyl group, a 3,3'-di-t-butyl-5,5'-dimethoxy-6,6'-dimethyl-1,1'-biphenyl-2,2'-diyl group, a 3,3'-di-t-butyl-5,5'-diethoxy-6,6'-dimethyl-1,1'-biphenyl-2,2'-diyl group, a 3,3'-di-t-butyl-5,5'-di-t-butoxy-6,6'-dimethyl-1,1'-biphenyl-2,2'-diyl group, a 3,3',5,5'-tetra(cyclooctyl)-6,6'-dimethyl-1,1'-biphenyl-2,2'diyl group, and a 3,3',5,5'-tetra-t-butyl-6,6'-dichloro-1,1'-biphenyl-2,2'-diyl group. It has heretofore been believed that a compound which is free from a steric hindrance of $R^1$ and $R^4$ in the formula (1) or (2) i.e. one having no substituent for $R^1$ and $R^4$, is thermally stable, as the molecular motion is easy. However, it has now been found surprisingly that by introducing substituents ($R^1$ and $R^4$) at the 6,6-positions of the bisarylene group as mentioned above, the thermal stability of the bisphosphite compound can further remarkably be improved. The reason for this improvement has not yet been clearly understood. However, it is considered that by the introduction of the substituents ($R^1$ and $R^4$) at the 6,6-positions, the free rotation of the two substituted phenyl groups about the carbon—carbon bond of the bisarylene group, is suppressed, whereby it tends to be difficult to have a conformation to initiate thermal decomposition.

The arylene group for each of $Ar^1$ to $Ar^4$ in the formula (1) or (2) is preferably a divalent arylene group wherein the carbon atoms bonding to the oxygen atom and Q or Q' in the formula, are adjacent to each other. Specifically, a substituted or unsubstituted phenylene or naphthylene group may be mentioned. The substituent may, for example, be a linear or branched alkyl group such as a methyl group, an ethyl group, a propyl group, an isopropyl group, a sec-butyl group, a t-butyl group, an octyl group, a nonyl group or a dodecyl group, a cycloalkyl group such as cyclohexyl group or a cyclooctyl group, an alkoxy group such as a methoxy group, an ethoxy group or a t-butoxy group, an aryl group such as a phenyl group, a tolyl group or a naphthyl group, an aralkyl group such as a benzyl group, an acyl group such as an acetyl group or a benzoyl group, an alkoxy carbonyl group, a cyano group, a nitro group, a halogen atom such as a fluorine atom, a chlorine atom, a bromine atom or an iodine atom, a silyl group such as a trimethyl silyl group, or a siloxy group such as a trimethyl siloxy group. The positions and the number of substituents are not particularly limited.

Each of $Z^1$ and $Z^2$ in the formula (2) may, for example, be a $C_{1-20}$ alkyl group, for example, a linear or branched alkyl group such as a methyl group, an ethyl group, a propyl group, an isopropyl group, a butyl group, a sec-butyl group, a t-butyl group, an octyl group, a nonyl group or a dodecyl group, a cycloalkyl group such as a cyclohexyl group or a cyclooctyl group, a substituted or unsubstituted aryl group such as a phenyl group, a naphthyl group, a p-methoxyphenyl group, a p-carbomethoxyphenyl group, a p-nitrophenyl group, a pentafluorophenyl group, a p-chlorophenyl group, a p-fluorophenyl group, an o-tolyl group, a m-tolyl group, a p-tolyl group, a p-nonylphenyl group, a p-trifluoromethylphenyl group, a p-perfluorobutylphenyl group, or an aralkyl group such as a benzyl group. Further, as each of $Z^1$ and $Z^2$, an aromatic group containing a hetero atom may be mentioned, which includes, for example, a 2-pyridyl group, a 3-pyridyl group, a 4-pyridyl group, a 4-methyl-2-pyridyl group, a 6-methyl-2-pyridyl group, a 3-nitro-2-pyridyl group, a 2-pyradyl group, a 4-pyrimidyl group, a 4-methyl-2-pyrimidyl group, a 4-benzofuryl group, a 5-benzofuryl group, a 5-benzothienyl group, a 2-quinolyl group, a 4-quinolyl group, a 6-quinolyl group, a 8-quinolyl group, a 5-nitro-8-quinolyl group, a 1-isoquinolyl group, a 3-isoquinolyl group, a 5-isoquinolyl group, a 2-quinoxalyl group, a 8-quinalzyl group, a 4-quinazolyl group, a 1-methyl-2-benzoimidazolyl group, a 2-benzothiazolyl group, an N-methyl-2-carbazolyl group, a 2-benzofuranyl group, an N-methyl-4-indolyl group, an N-methyl-5-indolyl group, and a 4-methoxy-9-acridinyl group. Among them, as $Z^1$ and $Z^2$, a substituted or unsubstituted aryl group is preferred.

Each of Q and Q' is a linking group such as —CH$_2$—, —CH(CH$_3$)—, —NH—, —N(CH$_3$)—, —Si(CH$_3$)$_2$—, —S—, —O— or —CO—. Each of n and n' is 0 or 1.

The bisphosphite of the formula (1) can be synthesized, for example, by the method disclosed in JP-A-62-116587.

Whereas, the bisphosphite of the formula (2) is a novel compound and can be prepared, for example, by the following method.

A 1,1'-biphenyl-2,2'-diol of the formula (I) and a chlorodiaryloxy phosphine of the formula (4) are reacted in rhe presence of a base in a solvent or without a solvent, then, PCl$_3$ is reacted thereto in the presence of a base, and further, $Z^1$-OH and $Z^2$-OH are reacted thereto in the presence of a base.

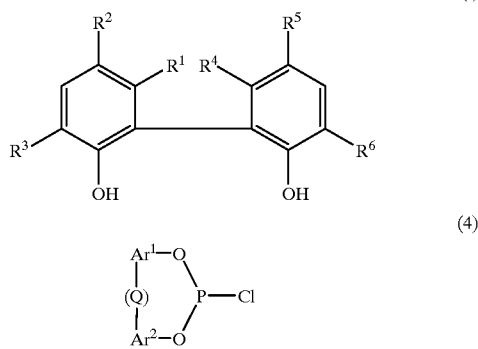

In the above formulae, $R^1$ to $R^6$, $Ar^1$, $Ar^2$, Q, n, $Z^1$ and $Z^2$ are as defined in formula (2).

The base to be used for the reaction may, for example, be a nitrogen-containing base such as pyridine, triethylamine or diethylamine or an inorganic base such as sodium carbonate or potassium carbonate. A nitrogen-containing base is preferably employed from the viewpoint of the easiness of the reaction operation. The base is used usually in an amount of 1 mol per mol of the compound of the formula (I). However, to carry out the subsequent reaction without cumbersome operation, it is preferred that the base is preliminarily incorporated in an amount of 4 mol or more per mol of the compound of the formula (I).

The reaction may be carried out within a temperature range of from −50° C. to 60° C., preferably from −30° C. to room temperature. The reaction time may be selected within a range of from 1 minute to 48 hours, but a reaction time of from 5 minute to 10 hours is preferred.

PCl$_3$ is added preferably in an amount of 1 mol per mol of the compound of the formula (I). The reaction may be carried out within a temperature range of from −50° C. to 60° C., preferably from −30° C. to room temperature. The reaction time can be selected within a range of from 1 minute to 48 hours, but a reaction time of from 5 minutes to 10 hours is preferred.

The above reaction product can be subjected to the subsequent operation without isolation or purification. It is reacted with alcohols or phenols represented by $Z^1$-OH and $Z^2$-OH. $Z^1$ and $Z^2$ are preferably the same. Each of $Z^1$-OH and $Z^2$-OH is used preferably in an amount of 1 mol per mol of the compound of the formula (I).

The reaction may be carried out within a temperature range of from −50° C. to 60° C., preferably from −30° C. to room temperature. The reaction time can be selected within a range of from 1 minute to 48 hours, but a reaction time of from 5 minutes to 10 hours is preferred.

As the solvent for reaction in the above mentioned series of operations, an ether such as tetrahydrofuran, diethyl ether or dioxane, a hydrocarbon such as hexane or toluene, a nitrogen-containing compound such as pyridine, triethylamine or N,N,N',N'-tetramethylethylenediamine, or a mixture thereof, may be used. Among them, an ether such as tetrahydrofuran, or a hydrocarbon solvent such as hexane or toluene, is preferred. A salt of the base with hydrogen chloride produced as a by-product along with the progress of the reaction, may be removed from the reaction system, if required, by a method such as filtration in an inert gas atmosphere such as a nitrogen atmosphere.

The obtained bisphosphite compound may be purified by a method such as chromatography, suspension washing by an organic solvent, or recrystallization.

As bisphosphite compound suitable for use as ligands for the hydroformylation reaction, those identified in the following Tables 1 and 2 may be mentioned. In the formulae, tBu represents a t-butyl group, iPr an i-propyl group, Et an ethyl group, and OMe a methoxy group.

TABLE 1

| Structural formula | No. |
|---|---|
| (structure with two tBu-substituted biphenyl rings bridged by methyl groups, with phosphite-biphenyl groups) | (1) |
| (structure with two tBu-substituted biphenyl rings bridged by ethyl groups, with phosphite-biphenyl groups) | (2) |
| (structure with two tBu-substituted biphenyl rings bridged by Cl groups, with phosphite-biphenyl groups) | (3) |
| (structure with two tBu-substituted biphenyl rings bridged by OMe groups, with phosphite-biphenyl groups) | (4) |

TABLE 1-continued

| Structural formula | No. |
|---|---|
| | (5) |
| | (6) |
| | (7) |
| | (8) |

TABLE 1-continued

| Structural formula | No. |
| --- | --- |
| (structure) | (9) |
| (structure) | (10) |
| (structure) | (11) |
| (structure) | (12) |

TABLE 1-continued

| Structural formula | No. |
|---|---|
| | (13) |
| | (14) |
| | (15) |
| | (16) |

TABLE 1-continued

| Structural formula | No. |
| --- | --- |
| | (17) |
| | (18) |
| | (19) |
| | (20) |

TABLE 1-continued
| Structural formula | No. |
|---|---|
| 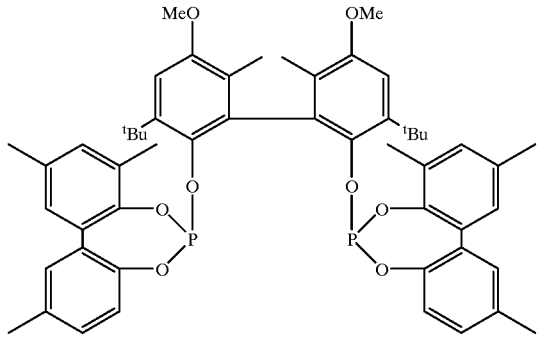 | (21) |
| 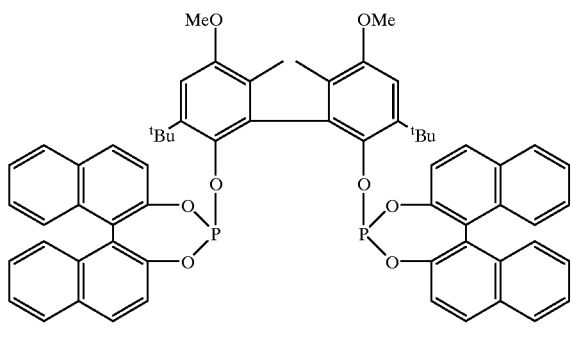 | (22) |
| 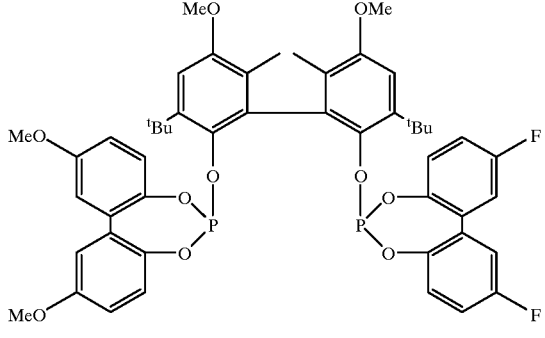 | (23) |
| 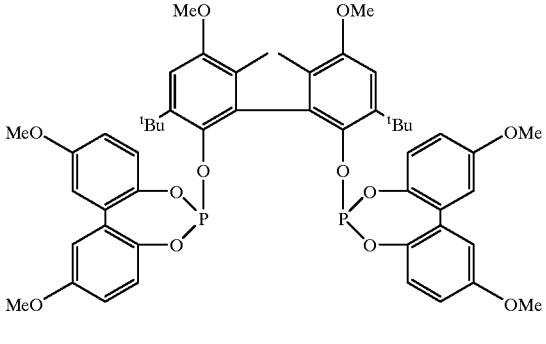 | (24) |

TABLE 1-continued

| Structural formula | No. |
| --- | --- |
| | (25) |
| | (26) |
| | (27) |
| | (28) |

TABLE 1-continued

| Structural formula | No. |
|---|---|
| | (29) |
| | (30) |
| | (31) |
| | (32) |

TABLE 1-continued

| Structural formula | No. |
| --- | --- |
| | (33) |
| | (34) |
| | (35) |

TABLE 2

| Structural formula | No. |
|---|---|
| | (36) |
| | (37) |
| | (38) |
| | (39) |

TABLE 2-continued

| Structural formula | No. |
| --- | --- |
| | (40) |
| | (41) |
| | (42) |
| | (43) |

TABLE 2-continued

| Structural formula | No. |
|---|---|
| | (44) |
| | (45) |
| | (46) |

TABLE 2-continued

| Structural formula | No. |
| --- | --- |
| | (47) |
| | (48) |
| | (49) |

TABLE 2-continued

| Structural formula | No. |
|---|---|
| | (50) |
| | (51) |
| | (52) |
| | (53) |

TABLE 2-continued

| Structural formula | No. |
|---|---|
| (structure) | (54) |
| (structure) | (55) |
| (structure) | (56) |

In the present invention, it is possible to satisfy a high reaction rate and, in some cases, excellent selectivity for the desired product simultaneously by carrying out the hydroformylation reaction of a mono-olefinic compound by using the bisphosphite compound of the formula (1) or (2) as a ligand.

The mono-olefinic compound to be used as the starting material in the hydroformylation reaction of the present invention, is not particularly limited, so long as it is an organic compound having one olefinic double bond in its molecule. Specifically, it may, for example, be ethylene, propylene, butene, pentene, hexene, octene, decene, hexadecene, octadecene, eicosene, docosene, styrene, α-methylstyrene, cyclohexene, a lower olefin mixture such as a propylene/butene mixture or a 1-butene/2-butene/isobutylene mixture, an olefinic hydrocarbon such as a mixture of olefin oligomer isomers such as dimer to tetramer of a lower olefin such as propylene, n-butene or isobutylene, or a polar group-substituted olefin such as acrylonitrile, allyl alcohol, oleyl alcohol, methyl acrylate, methyl methacrylate, methyl oleate or methyl 3-pentenoate. Among them, it is preferred to use a $C_{3-10}$ mono-olefinic compound.

The Group VIII metal compound as the catalyst or its precursor for the hydroformylation reaction, may, for example, be a hydride, a halide, an organic salt, an inorganic salt, an oxide, a carbonyl compound, an amine compound, an olefin-coordinated compound, a phosphine-coordinated compound or a phosphite-coordinated compound of a Group VIII metal. For example, it may be a ruthenium compound such as ruthenium trichloride, tetraamminehydroxychlororuthenium chloride or dichlorotris(triphenylphosphine)ruthenium, a palladium compound such as palladium acetate or palladium chloride, an osmium compound such as osmium trichloride, an iridium compound such as iridium trichloride or iridium carbonyl, a platinum compound such as platinic acid, sodium hexachloroplatinate or potassium platinate, or a cobalt compound such as dicobalt octacarbonyl or cobalt stearate, or a rhodium compound such as rhodium trichloride, rhodium nitrate, rhodium acetate, Rh(acac)(CO)$_2$, [Rh(OAc)(COD)]$_2$, Rh$_4$(CO)$_{12}$, Rh$_6$(CO)$_{16}$, HRh(CO)(PPh$_3$)$_3$, [Rh(OAc)(CO)$_2$]$_2$, [Rh($\mu$-S(t-Bu))(CO)$_2$]$_2$ or [RhCl(COD)]$_2$ wherein acac represents an acetylacetonate group, OAc an acetoxy group, COD 1,5-cyclooctadiene, Ph a phenyl group and t-Bu a t-butyl group. However, the Group VIII metal compound is not limited to such specific examples. Among them, preferred is a cobalt, rhodium or ruthenium compound, and particularly preferred is a rhodium compound.

In the process of the present invention, the bisphosphite compound may be used as preliminarily permitted to form a complex with the above Group VIII metal compound. The Group VIII metal complex containing the bisphosphite compound can readily be prepared by a conventional method for forming a complex from a Group VIII metal compound and the bisphosphite compound. In some cases, the Group VIII metal compound and the bisphosphite compound may be separately supplied to the hydroformylation reaction zone to form the complex there.

The amount of the Group VIII metal compound is not particularly limited, and there is a limit from the viewpoint of the catalytic activity and the economical feasibility. It is usually selected so that the concentration in the hydroformylation reaction zone is within a range of from 0.05 mg to 5 g, preferably from 0.5 mg to 1 g, per 1 liter of the solvent for the reaction or the olefinic compound, as calculated as the metal atoms.

The amount of the bisphosphite compound of the present invention is not particularly limited, and it is suitably set so that good results are obtainable with respect to the catalytic activity and the selectivity. It is selected usually within a range of from about 0.001 to 500 mols, preferably from 0.1 to 100 mols, more preferably from 0.5 to 50 mols, per mol of the Group VIII metal.

Use of a solvent for the reaction is not essential for the hydroformylation reaction. However, a solvent inert to the hydroformylation reaction may be used as the case requires. Specific examples of preferred solvents include aromatic hydrocarbon compounds such as toluene, xylene and dodecylbenzene, ketones such as acetone, diethyl ketone and methyl ethyl ketone, ethers such as tezrahydrofurane and dioxane, esters such as ethyl acetate and di-n-octylphthalate, high boiling components produced as by-products during the hydroformylation reaction, such as condensation products of aldehyde, and the olefinic compound as the material for the reaction. Among them, toluene or xylene is preferred from the viewpoint that the solubility of the oxo gas increases, and an aldehyde condensate is preferred from the viewpoint that it is not required to add it anew.

The conditions for the hydroformylation reaction in the present invention may be the same as those commonly employed for reactions of this type. Namely, the reaction temperature is selected usually within a range of from 15 to 200° C., preferably from 50 to 150° C., and the CO partial pressure and the H$_2$ partial pressure are selected usually within a range of from 0.001 to 200 atm, preferably from 0.1 to 100 atm, more preferably from 1 to 50 atm. The molar ratio of hydrogen to carbon monoxide (H$_2$/CO) is selected usually within a range of from 10/1 to 1/10, preferably from 1/1 to 1/6. The hydroformylation reaction system may be a continuous system, or a batch system which may be conducted, for example, in an agitation type reactor or a bubbling column type reactor. The bisphosphite compound of the present invention is thermally stable, and it is preferred to employ a continuous system, whereby the present invention is particularly effective.

In the reaction product solution, in addition to the desired aldehyde product, unreacted materials, the solvent, medium boiling point and high boiling point by-products are present. The medium boiling point by-products mean compounds having boiling points lower than the bisphosphite compound and are those formed mainly by secondary side reactions of aldehydes formed by the hydroformylation reaction. For example, in the hydtroformylation reaction of propylene, linear n-butyl aldehyde and branched isobutyl aldehyde will be formed, and these aldehyde products are highly reactive and gradually undergo a polymerization or condensation reaction by themselves in the absence of a catalyst even at a relatively low temperature to form medium boiling point poly condensation products. For example, with respect to n-butyl aldehyde, a dimer and a trimer as its self-polymerization products, 2-ethylhexenal as its condensation dimer, 2-ethylhexanal and 2-ethylhexanol as hydrogenated products thereof, and n-butanol and dibutyl acetal as hydrogenated products of n-butyl aldehyde, may be mentioned. Further, from isobutyl aldehyde, its dimer and trimer will be formed by a reaction similar to the reaction of n-butyl aldehyde, and further, a dimer, a trimer and their derivatives as alternate polymerization products of n-butyl aldehyde and isobutyl aldehyde, will also be formed.

Further, in addition to these medium boiling point by-products, high boiling point by-products having boiling points higher than the bisphosphite compound, will also be formed by side reactions.

In the present invention, it is preferred that after separating at least one member of the above mentioned components from the reaction product solution after the hvdroformylation reaction, a recovered liquid containing at least the Group VIII metal compound and the bisphosphite compound, is recycled to the reaction system. As a means to separate at least one member of these components from the reaction product solution, any separation operation commonly used in a conventional liquid catalyst recycling process may be employed. Specifically, in addition to a distillation operation such as simple distillation, reduced pressure distillation, thin membrane distillation or steam distillation, gas-liquid separation, evaporation, gas stripping, gas absorption or extraction, may, for example, be mentioned. The respective separation operations may be carried out in separate independent steps, or separation of two or more components may be carried out simultaneously.

The bisphosphite compound to be used in the process of the present invention is excellent in the stability, particularly in the thermal stability, as substituents (R$^1$ and R$^4$) are introduced to the 6,6'-positions of the bisarylene group. Accordingly, in the above mentioned separation operations, the bisphosphite compound can be present in a sufficiently stable state. The temperature for the above mentioned separation operations is selected usually within a range of at most 200° C., preferably from 50 to 150° C. As the separation operation, separation by distillation or evaporation is preferred. Particularly preferred is distillation. Separation by distillation can be carried out, for example, in such a manner that the entire amount or a part of the reaction solution containing the formed aldehydes, the Group VIII metal catalyst and the bisphosphite compound, is withdrawn from the hydroformylation reaction zone, and preferably after separating carbon monoxide, hydrogen and, in some cases, an unreacted starting olefinic compound, introduced into a distillation column continuously or intermittently, whereby in the distillation column, the aldehyde products are distilled under atmospheric pressure, reduced pressure or elevated pressure, in one step or in a plurality of steps to recover the entire amount or a part of the aldehyde products. The vaporized or distilled aldehyde products thus separated, can be condensed and recovered by an optional conventional method. The distillation for separating the desired aldehyde products from the liquid reaction medium containing a part of the formed aldehydes, the Group VIII metal catalyst and the bisphosphite compound, can be carried out at a desired optional temperature, although it may depend substantially on the boiling point of the formed aldehydes. Usually, such distillation can be carried out at a temperature lower than 180° C., preferably lower than 150° C., more preferably from about 50° C. to about 130° C. For the distillation of high boiling point aldehyde products, it is advisable to carry out the distillation under reduced pressure. Usually, the distillation can be carried out under a reduced pressure of from 755 mmHg to 1 mmHg, preferably from 750 mmHg to 5 mmHg. The bisphosphite compound of the formula (1) or (2) of the present invention has a characteristic such that at the above mentioned preferred distillation temperature, decomposition or modification can be suppressed to the minimum level.

The reaction solution containing the Group VIII metal catalyst compound and the bisphosphite compound, remaining after separating at least one component of the products from the reaction product solution, can be recycled partly or in its entire amount to the reaction zone by an optional conventional method and subjected to the hydroformylation reaction again. As the temperature condition for this recycling of the reaction solution to the hydroformylation reaction, it is preferred to employ a temperature not substantially different from the temperature for the hydroformylation reaction, specifically a temperature within a range of from 50 to 150° C., from the viewpoint that no apparatus for recovery of the reaction heat is required.

Now, the present invention will be described in further detail with reference to Examples and Comparative Examples. However, it should be understood that the present invention is by no means restricted to such specific Examples. The bisphosphite No. used in Examples corresponds to No. in Table 1 or 2.

EXAMPLE 1

Calculation of the Structure of Bisphosphite (1)

Figure 6:
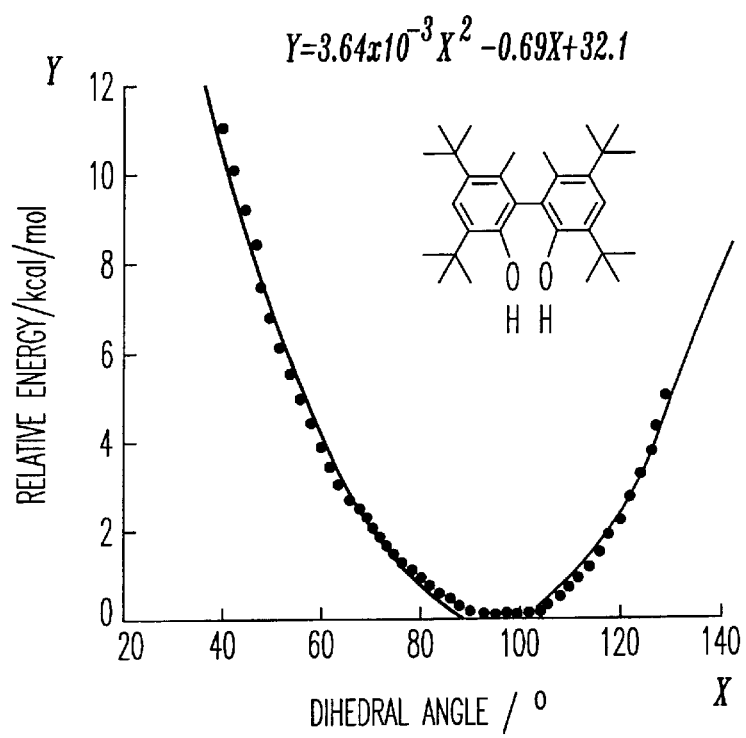
FIG. 6 is a graph showing the relation between the dihedral angle X and the relative energy Y with a model structure of the formula (I-1) in Example 1.
Figure 7:
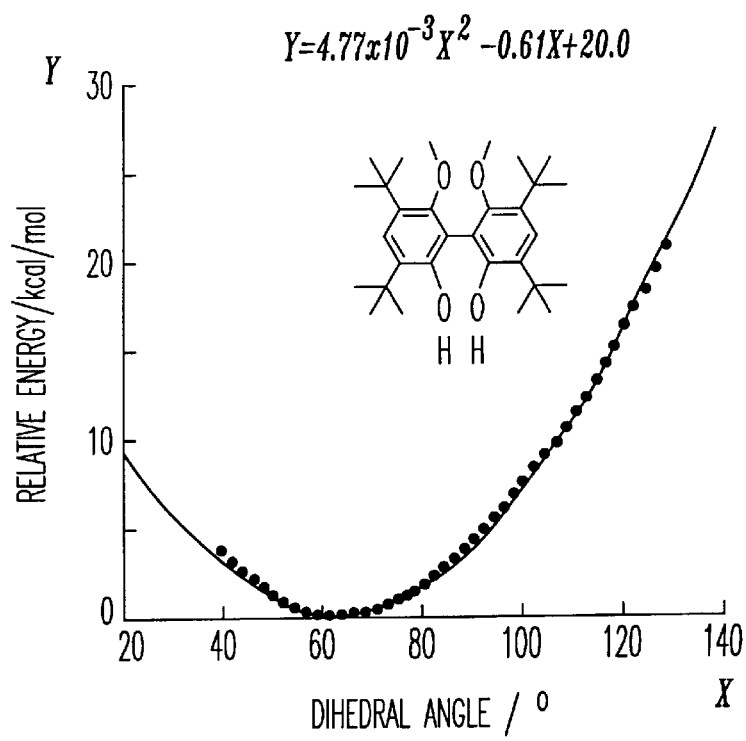
FIG. 7 is a graph showing the relation between the dihedral angle X and the relative energy Y with a model structure which corresponds to the formula (I-1) in Example 1 except that methyl groups at the 6,6-positions in the formula (I-1) are substituted by methoxy groups.
Figure 8:
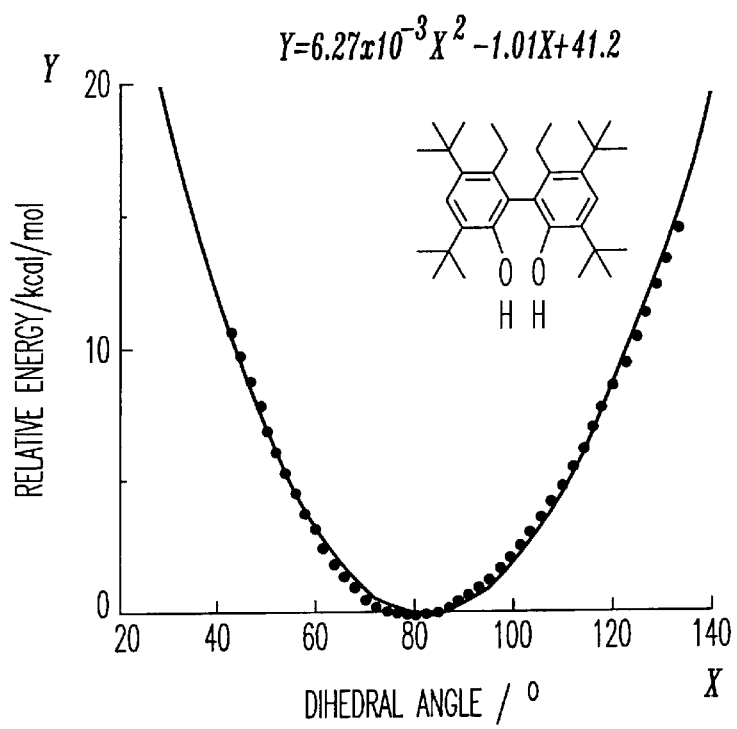
FIG. 8 is a graph showing the relation between the dihedral angle X and the relative energy Y with a model structure which corresponds to the formula (I-1) in Example 1 except that methyl groups at the 6,6-positions in the formula (I-1) are substituted by ethyl groups.
Figure 9:
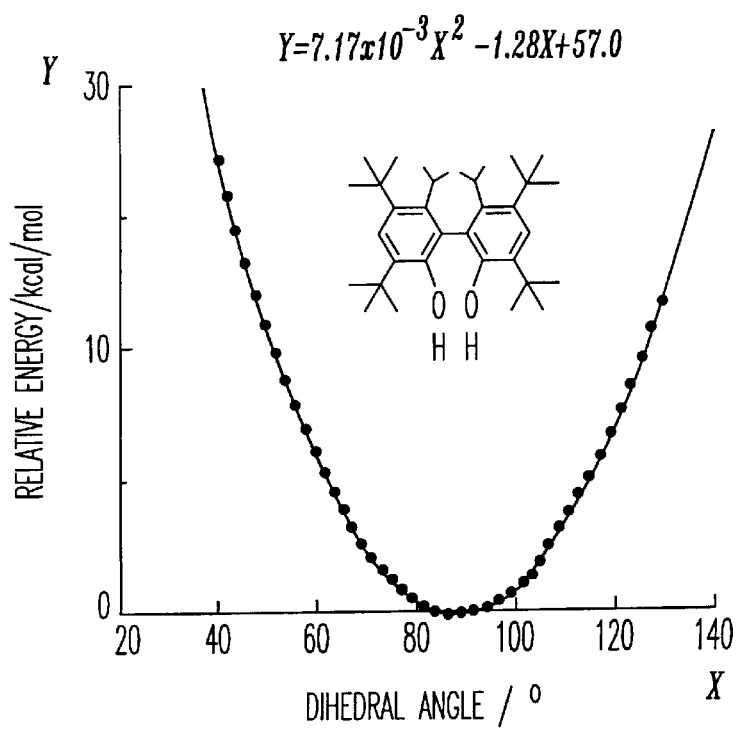
FIG. 9 is a graph showing the relation between the dihedral angle X and the relative energy Y with a model structure which corresponds to the formula (I-1) in Example 1 except that methyl groups at the 6,6-positions in the formula (I-1) are substituted by isopropyl groups.
Figure 10:
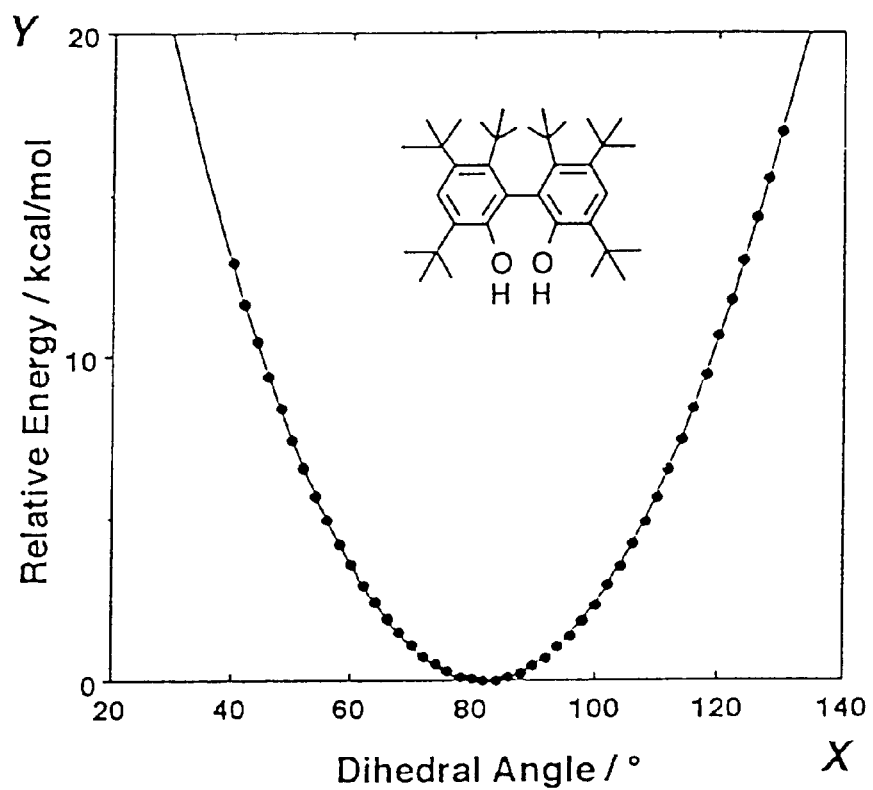
FIG. 10 is a graph showing the relation between the dihedral angle X and the relative energy Y with a model structure which corresponds to the formula (I-1) in Example 1 except that methyl groups at the 6,6-positions in the formula (I-1) are substituted by tert-butyl groups.

With respect to the bisphenylene structural moiety as the crosslinking structure of the following bisphosphite No. 1, a structure of the following formula (I-1) was set as a model, and by the following calculation method, energy values were calculated by changing the dihedral angle X between the two aromatic rings in the formula (I-1) within a range of from 130 to 40 degrees, and relative energy values Y were calculated by subtracting the lowest calculated energy value from the energy values at the respective dihedral angles. The relation between this dihedral angle X and the relative energy value Y, was plotted and shown in FIG. 6. Here, X and Y were represented by an approximate formula of $Y=3.64\times10^{-3}X^2-0.69X+32.1$.

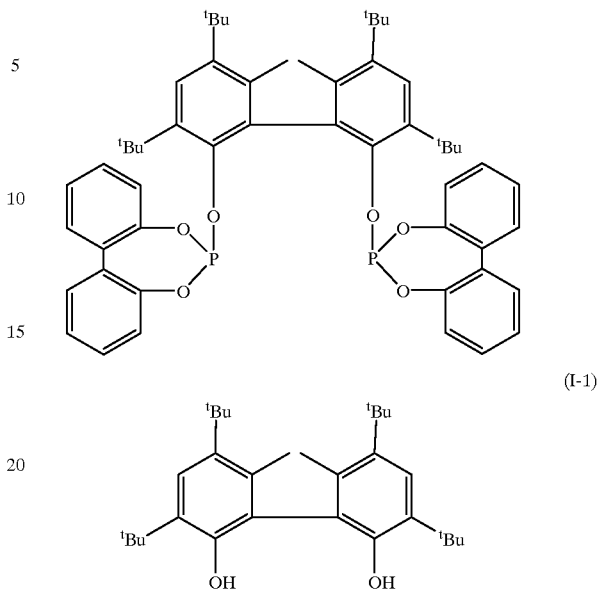

Calculation Method
  Calculation method: Molecular Mechanics Method
  Program: CAChe Mechanics Release 3.9
  Details of calculation: Optimization Method: Block-Diagonal
    Newton Raphson Method
    Converging condition: 0.001 kcal/mol.
  Computer: Power Machintosh 9500/120 system soft ware J1-7.5.5.

Hydroformylation Reaction

The interior of a thoroughly dried stainless steel autoclave of up and down stirring type having an internal capacity of 200 ml, was flushed three times with dry nitrogen. A catalyst mixed solution comprising 55 ml of toluene (as a solvent), 5 ml of n-heptane (as a GC internal standard), 3.94 mg of [Rh(OAc)(COD)]$_2$ and 50.6 mg of bisphosphite No.1 (P/Rh mol ratio: 8.0) separately prepared under nitrogen atmosphere, was injected into the autoclave by nitrogen pressure, and the autoclave was sealed. The interior of the autoclave was substituted by 20 kg/cm$^2$G of nitrogen gas, and then the nitrogen gas was released to 0 kg/cm$^2$G. Then, 4.5 g of propylene was injected thereto. The temperature was raised to 70° C., and synthesis gas (H$_2$/CO=1, partial pressure: 5.0 kg/cm$^2$) was immediately injected so that the total pressure in the autoclave became 9 kg/cm$^2$G inclusive of the pressure of propylene itself, to initiate the reaction. The reaction was continued for 84 minutes while synthesis gas consumed during the reaction was supplemented by a pressure accumulator via a secondary pressure controller to always maintain the total pressure in the reactor at a level of 9 kg/cm$^2$G. After completion of the reaction, the reactor was cooled to room temperature, and the gas phase and the liquid phase in the autoclave were collected and subjected to analyses of the respective components by means of gas chromatography. The reaction rate constant (k) was 1.29/hr. The $^{31}$P-NMR measurement of the reaction solution was carried out, whereby no signal attributable to the decomposed product of the ligand, was observed.

Comparative Example 1

Calculation of the Structure of a Bisphosohite

With respect to the following bisphosphite disclosed in JP-A-6-199728, in the same manner as in Example 1, relative energy values Y were calculated by changing the dihedral angle X between the two aromatic rings within a range of from 130 to 40 degrees. This relation between the dihedral angle X and the relative energy value Y was plotted and shown in FIG. 3. Here, X and Y were represented by an approximate formula of $Y=2.90\times10^{-4}X^2-6.34\times10^{-2}+3.68$.

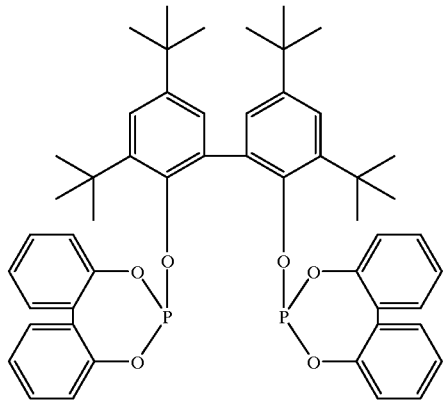

Hydroformylation Reaction

The hydroformylation reaction was carried out in the same manner as in Example 1 except that as the bisphosphite, the compound having the above structure was used in an amount of 48.9 mg (P/Rh mol ratio: 8.0), and the reaction time was changed to 90 minutes. As a result, the reaction rate constant (k) was 1.65/hr. The $^{31}$P-NMR measurement of the reaction solution was carried out, whereby no signal attributable to the decomposition product of the ligand, was observed.

EXAMPLE 2

Thermal Stability Test

The interior of the thoroughly dried stainless steel autoclave of top and bottom stirring type having an internal capacity of 200 ml, was flushed three times with dry nitrogen. A catalyst mixed solution comprising 60 ml of toluene (as a solvent), 78.8 mg of [Rh(OAc)(COD)]$_2$ and 1.01 g of bisphosphite No.1 (P/Rh mol ratio: 8.0) separately prepared under a nitrogen atmosphere, was injected to the autoclave by nitrogen pressure, and the autoclave was sealed. Synthesis gas (H$_2$/CO=1/1) was injected to the reactor so that the pressure became 9 kg/cm$^2$G, and the reactor was heated to 70° C., followed by stirring at this temperature for 30 minutes. After cooling to room temperature, synthesis gas was purged. Then, the interior of the reactor was flushed three times under nitrogen pressure of 10 kg/cm$^2$G to substitute synthesis gas in the solution and synthesis gas in the system by nitrogen and to bring the interior of the reactor to a nitrogen gas pressure of 0.5 kg/cm$^2$G. Then, the reactor was heated to 130° C., and heating and stirring were continued for a predetermined period of time. After cooling to room temperature, synthesis gas (H$_2$/CO=1/1) was injected under a pressure of 9.0 kg/cm$^2$ and again heated at 70° C. for 30 minutes. After cooling to room temperature, the interior of the system was similarly flushed with nitrogen, followed by heating to 130° C. and heating was continued at a predetermined temperature. This operation was repeated so that heating was carried out in a total of 48 hours at 130° C., whereby the relation between the degree of decomposition of the ligand and the temperature was examined by carrying out the $^{31}$P-NMR measurements. Further, the $^{31}$P-NMR measurements were carried out in such a manner that after treating with synthesis gas, the reaction solution was sampled under a nitrogen atmosphere and the measurement was carried out under a nitrogen atmosphere. The results at the respective times are shown in Table 3. The values in the Table represent the proportions relative to all the observed peaks.

TABLE 3

| Time | 8 hours | 48 hours |
| --- | --- | --- |
| Free ligand (1) (%) | 60.6 | 51.0 |
| Rh-(1) complex (%) | 3.1 | 11.4 |
| Amount of decomposition products (%) | 36.3 | 37.7 |
| Average decomposition ratio (%/hr) | 4.54 | 0.79 |

Comparative Example 2

The operation was carried out in the same manner as in Example 2 except that instead of the bisphosphite used in Example 2, the bisphosphite used in Comparative Example 1, was used in an amount of 0.979 g (P/Rh=8.0). The results are shown in Table 4.

TABLE 4

| Time | 8 hours | 48 hours |
| --- | --- | --- |
| Free ligand (1) (%) | 51.5 | 28.4 |
| Rh-(1) complex (%) | 4.0 | 4.8 |
| Amount of decomposition products (%) | 44.5 | 66.8 |
| Average decomposition ratio (%/hr) | 5.56 | 1.39 |

From the results of Example 1 and Comparative Example 1, it is evident that with respect to the reaction rate constant, high values which are substantially equal were accomplished in both Example 1 and Comparative Example 1. On the other hand, in the thermal stability test (Example 2 and Comparative Example 2) simulating the actual reaction process, the ligand in Example 2 showed no substantial change in the amount of the decomposed product of the ligand between 8 hours and 48 hours, and the decomposition substantially reached saturation after 48 hours. Whereas, with the ligand of Comparative Example 2, after 48 hours, the amount of the decomposed product further increased, thus indicating that it is unstable in a process where it is exposed at a high temperature for a long period of time. Namely, it is evident that the ligand of the present invention is an excellent ligand also from the industrial viewcoint, as it satisfies both a high reaction rate and high thermal stability in the entire process.

REFERENCE EXAMPLE

The calculation was carried out in the same manner as in Example 1 except that the substituents at the 6,6'-positions in the formula (I-1) were changed from methyl to various substituents, and the results obtained for the relation between the dihedral angle X and the relative energy value Y, are shown in Table 5. Further, the relations between X and Y were plotted and shown in FIGS. 3 to 10.

TABLE 5

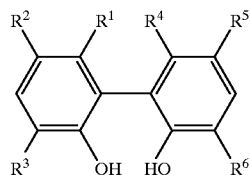

| S | Y = AX² + BX + C |
|---|---|
| H | Y = 2.90 × 10⁻⁴X² − 6.34 × 10⁻²X + 3.68 |
| F | Y = 1.31 × 10⁻³X² − 0.24X + 11.1 |
| Cl | Y = 3.55 × 10⁻³X² − 0.64X + 28.6 |
| CH3 | Y = 3.64 × 10⁻³X² − 0.69X + 32.1 |
| OCH3 | Y = 4.77 × 10⁻³X² − 0.61X + 20.0 |
| C2H5 | Y = 6.27 × 10⁻³X² − 1.03X + 41.2 |
| ⁱPr | Y = 7.17 × 10⁻³X² − 1.28X + 57.0 |
| ᵗBu | Y = 7.32 × 10⁻³X² − 1.20X + 49.2 |

Figure 3:
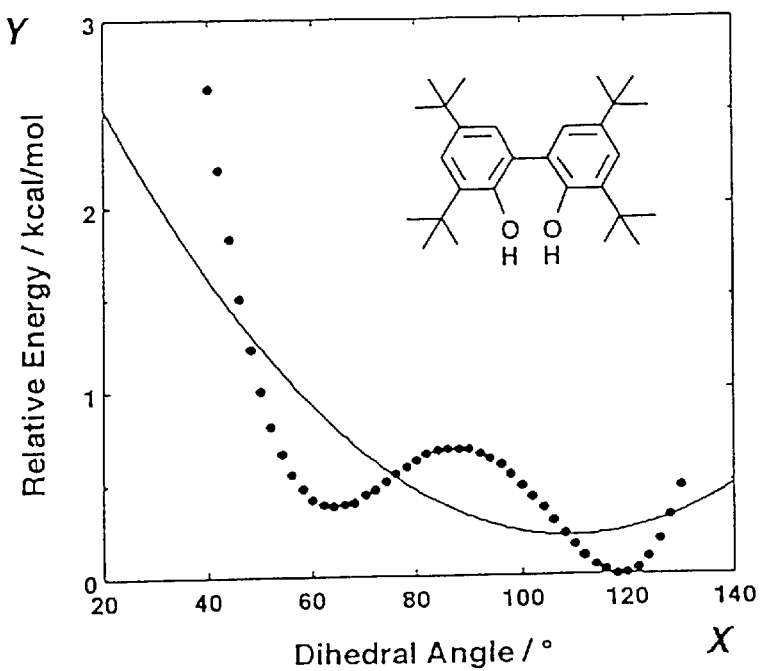
FIG. 3 is a graph showing the relation between the dihedral angle X and the relative energy Y with a model structure which corresponds to the formula (I-1) in Example 1 except that methyl groups at the 6,6-positions in the formula (I-1) are substituted by hydrogen atoms.
Figure 4:
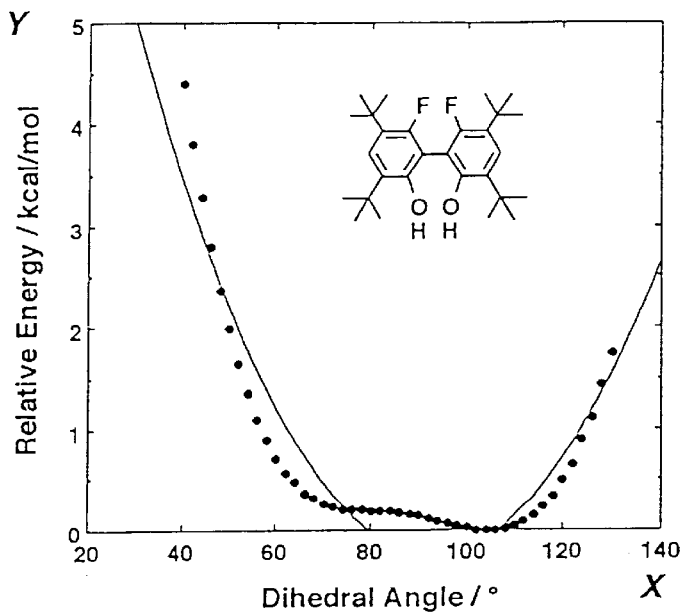
FIG. 4 is a graph showing the relation between the dihedral angle X and the relative energy Y with a model structure which corresponds to the formula (I-1) in Example 1 except that methyl groups at the 6,6-positions in the formula (I-1) are substituted by fluorine atoms.
Figure 5:
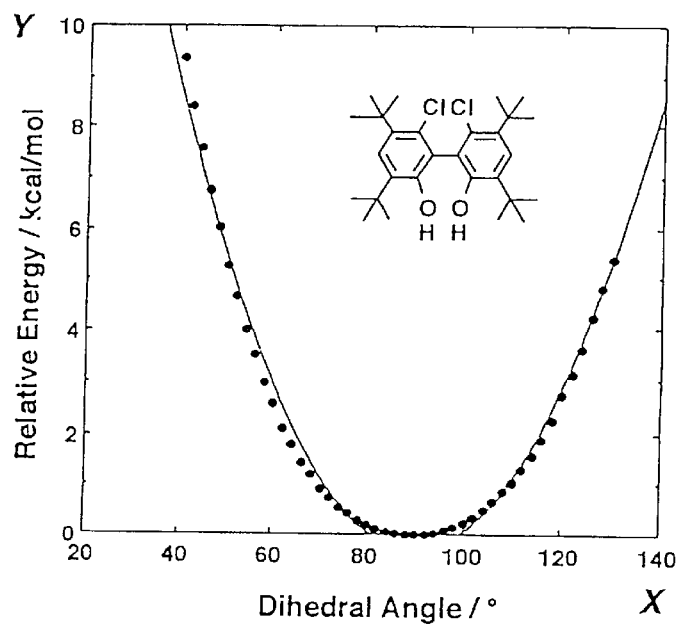
FIG. 5 is a graph showing the relation between the dihedral angle X and the relative energy Y with a model structure which corresponds to the formula (I-1) in Example 1 except that methyl groups at the 6,6-positions in the formula (I-1) are substituted by chlorine atoms.

When FIG. 3 is compared with FIGS. 4 to 10, it is evident that in each of FIGS. 4 to 10, the relation between the energy and the dihedral angle X of the aromatic rings describes a smooth parabola, and it tends to hardly take an unstable steric structure to induce the decomposition of the ligand. Whereas, in FIG. 3, the molecular structure is likely to change and is likely to change also to the unstable structure.

As described in the foregoing, the bisphosphite of the formula (1) or (2) having a specific structure of the present invention is excellent in thermal stability as compared with conventional bisphosphites, and it can be recovered in good yield during the reaction or in a step after the reaction and can be recycled for reuse in the reaction.

What is claimed is:

1. A process for producing aldehydes, which comprises reacting an olefinic compound consisting essentially of a mono-olefinic compound with carbon monoxide and hydrogen in the presence of a Group VIII transition metal compound, wherein the reaction is carried out in the presence of a bisphosphite compound of the following formula (1) or (2) having a bisphenylene structural moiety connecting the two phosphite structures, said bisphenylene structural moiety being represented by a structure of the following formula (I)

(I)

$R^2 \quad R^1 \quad R^4 \quad R^5$ $R^3 \quad OH \quad HO \quad R^6$ and when, by the following calculation method;
Calculation method:
  Molecular Mechanics Method
  Program: CAChe Mechanics Release 3.9
  Details of calculation: Optimization Method: Block Diagonal
    Newton Raphson Method
    Converging condition: 0.001 kcal/mol
  using a dihedral angle between the two aromatic rings of the structure of the formula (I) as a variable X (degrees), energy values are calculated by changing the dihedral angle X within a range of from 130 to 40 degrees, and relative energy values Y (kcal/mol) are calculated by subtracting the lowest calculated energy value from the energy values at the respective dihedral angles, and the relation between the dihedral angle X and the relative energy value Y is represented by the formula Y=AX²+BX+C, coefficient A satisfies A≧5× 10⁻⁴:

(1)

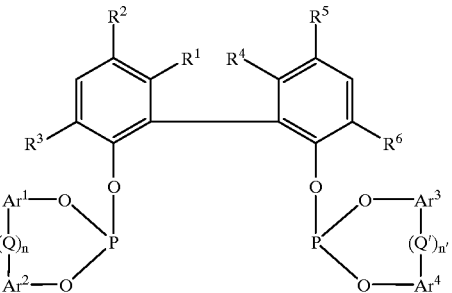

wherein each of $R^1$ to $R^6$ which are independent of one another, is a group selected from the group consisting of a hydrogen atom, an alkyl group, a cycloalkyl group, an alkoxy group, a silyl group, a siloxy group, an alkoxy carbonyl group, an acyl group, a —SO₃Na group, a —SO₃Li group, a —COONa group, a fluorine atom, a chlorine atom, a bromine atom and an iodine atom, with the proviso that $R^1$ and $R^4$ are not hydrogen, each of $Ar^1$, $Ar^2$, $Ar^3$ and $Ar^4$ which are independent of one another, is a substituted or unsubstituted arylene group, each of Q and Q' which are independent of each other, is a linking group selected from the group consisting of —CR⁷R⁸—, —O—, —S—, —NR⁹—, SiR¹⁰R¹¹— and —CO—, wherein each of $R^7$ to $R^{11}$ which are independent of one another, is a hydrogen atom, a $C_{1-12}$ alkyl group or an aryl group, and each of n and n' which are independent of each other, is 0 or 1, (2)

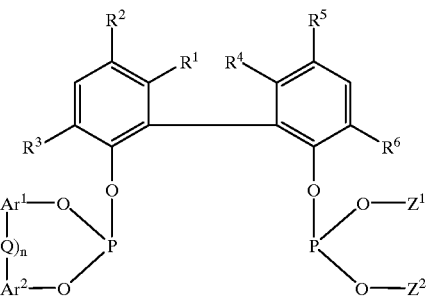

wherein $R^1$ to $R^6$, $Ar^1$ to $Ar^2$, Q and n are as defined in the formula (1), each of $Z^1$ and $Z^2$ which are independent of each other, is a $C_{1-20}$ alkyl group, a cycloalkyl group, a substituted or unsubstituted aryl group, an aralkyl group or a hetero aryl group.

2. The process for producing aldehydes according to claim 1, wherein the reaction is carried out in the presence of a bisphosphite compound wherein the coefficient A satisfies 1.00×10⁻³≦A≦1.00×10⁻².

3. A process for producing aldehydes, which comprises reacting an olefinic compound consisting essentially of a mono-olefinic compound with carbon monoxide and hydrogen in the presence of a Group VIII transition metal compound, wherein the reaction is carried out in the presence of a bisphosphite compound of the following formula (1) or (2):

(1)

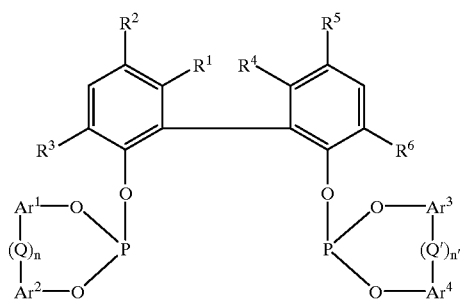

wherein each of $R^1$ and $R^4$ which are independent of each other, is a $C_{1-12}$ alkyl group, a cycloalkyl group, an alkoxy group, a silyl group, a siloxy group, an alkoxy carbonyl group, an acyl group, a —$SO_3Na$ group, a —$SO_3Li$ group, a —COONa group or a halogen atom, each of $R^2$, $R^3$, $R^5$ and $R^6$ which are independent of one another, is a hydrogen atom, a $C_{1-20}$ alkyl group, a cycloalkyl group, an alkoxy group, an aryl group, a silyl group or a siloxy group, each of $Ar^1$, $Ar^2$, $Ar^3$ and $Ar^4$ which are independent of one another, is a substituted or unsubstituted arylene group, each of Q and Q' which are independent of each other, is a linking group selected from the group consisting of —$CR^7R^8$—, —O—, —S—, $NR^9$—, —$SiR^{10}R^{11}$— and —CO—, wherein each of $R^7$ to $R^{11}$ which are independent of one another, is a hydrogen atom, a $C_{1-12}$ alkyl group or an aryl group, and each of n and n' which are independent of each other, is 0 or 1, (2)

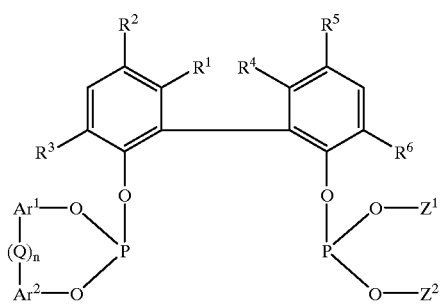

wherein $R^1$ to $R^6$, $Ar^1$, $Ar^2$, Q and n are as defined in the formula (1), each of $Z^1$ and $Z^2$ which are independent of each other, is a $C_{1-20}$ alkyl group, a cycloalkyl group, a substituted or unsubstituted aryl group, an aralkyl group or a hetero aryl group.

4. The process for producing aldehydes according to claim 3, wherein in the formula (1) or (2), each of $R^1$ and $R^4$ is a $C_{1-3}$ alkyl or alkoxy group, or a halogen atom.

5. The process for producing aldehydes according to claim 4, wherein in the formula (1) or (2), each of $R^1$ and $R^4$ is a methyl group or a methoxy group.

6. The process for producing aldehydes according to claim 3, wherein in the formula (1) or (2), each of $R^2$, $R^3$, $R^5$ and $R^6$ which are independent of one another, is a $C_{3-20}$ branched alkyl group or a cycloalkyl group.

7. The process for producing aldehydes according to claim 3, wherein in the formula (1) or (2), each of $Ar^1$ to $Ar^4$ which are independent of one another, is a substituted or unsubstituted phenylene or naphthylene group.

8. The process for producing aldehydes according to claim 3, wherein the mono-olefinic compound is reacted with carbon monoxide and hydrogen in the presence of the Group VIII transition metal compound and the bisphosphite compound of the formula (1) or (2), and from the reaction product solution, at least one component selected from carbon monoxide, hydrogen, an unreacted mono-olefinic compound, an aldehyde product, a solvent, a medium boiling point by-product and a high boiling point by-product, is separated by a separation operation, and a reaction solution containing at least the Group VM transition metal compound and the bisphosphite compound, is recycled to the reaction system.

9. The process for producing aldehydes according to claim 3, wherein the reaction is carried out in the presence of the bisphosphite compound of the formula (1).

10. The process for producing aldehydes according to claim 3, wherein the reaction is carried out in the presence of the bisphosphite compound of the formula (2).

11. The process for producing aldehydes according to claim 10, wherein in the formula (2), each of $Z^1$ and $Z^2$ which are independent of each other, is a substituted or unsubstituted aryl group.

* * * * *